United States Patent [19]
Mark

[11] 4,210,765
[45] Jul. 1, 1980

[54] PROCESS FOR OBTAINING HALOGENATED DIPHENOLS

[75] Inventor: Victor Mark, Evansville, Ind.

[73] Assignee: General Electric Company, Pittsfield, Mass.

[21] Appl. No.: 882,242

[22] Filed: Feb. 28, 1978

[51] Int. Cl.$^2$ .................. C07C 39/16; C07C 37/00
[52] U.S. Cl. .................................. 568/726; 260/395; 568/33; 568/37; 568/48; 568/74; 568/717; 568/718; 568/719; 568/722; 568/729; 568/730; 568/637
[58] Field of Search .............. 568/726, 718, 722, 637, 568/717, 719, 729, 730; 260/395, 607 AR, 609 F, 607 B

[56] References Cited

U.S. PATENT DOCUMENTS

| 2,254,904 | 9/1941 | Moss | 568/726 |
|---|---|---|---|
| 2,902,518 | 9/1959 | Hurdis et al. | 568/726 |
| 3,143,575 | 8/1964 | Bryner et al. | 568/726 |
| 3,903,175 | 9/1975 | Meyer | 568/726 |
| 3,932,535 | 1/1976 | Zoche et al. | 568/726 |
| 4,075,119 | 2/1978 | Schmidt et al. | 568/726 |

FOREIGN PATENT DOCUMENTS 232980 12/1968 U.S.S.R. .............................. 568/726

Primary Examiner—Norman Morgenstern
Attorney, Agent, or Firm—Salvatore C. Mitri; William F. Mufatti

[57] ABSTRACT

An improved process for obtaining halogenated diphenols which can be pure dihalodiphenols or predetermined, statistical mixtures comprising unreacted diphenol, monohalodiphenols and dihalodiphenols.

8 Claims, 1 Drawing Figure

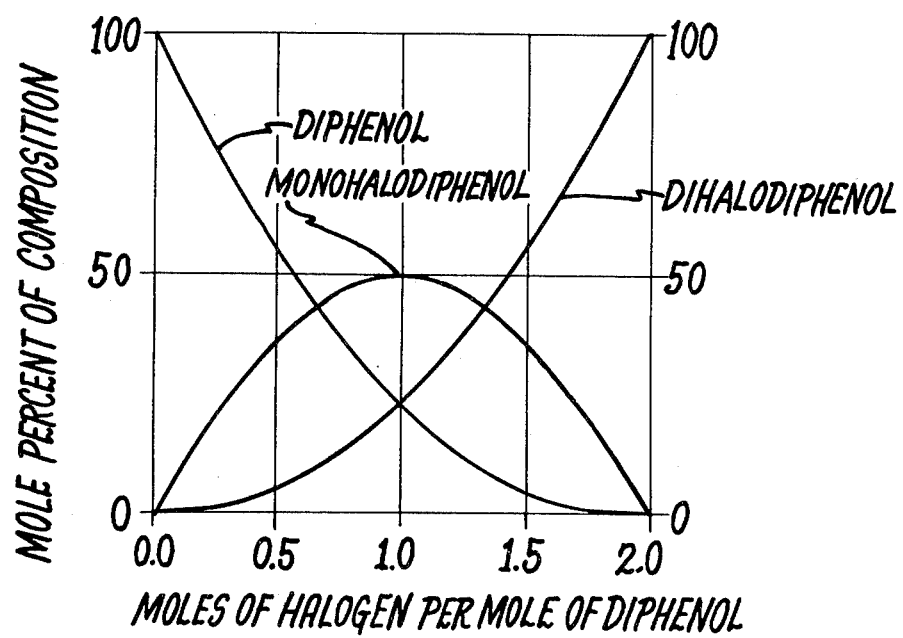

PROCESS FOR OBTAINING HALOGENATED DIPHENOLS

This invention relates to an improved process for obtaining halogenated diphenols. More particularly, this invention relates to an improved process that permits the reaction to be closely controlled enabling pure dihalodiphenols or predetermined, statistical mixtures of halogenated diphenols to be obtained.

BACKGROUND OF THE INVENTION

It is known to prepare halogenated diphenols which can be used as anti-mildew agents, fungicides, fire retardant agents in various polyesters, monomers for the preparation of aromatic polycarbonates, and the like.

The preparation of halophenols, including halodiphenols, halotriphenols, halotetraphenols, etc., is often desired to improve the properties of the parent phenol. For instance, the halogenated phenols often possess enhanced, desirable biological properties, compared with nonhalogenated phenols and have been manufactured on a large scale. For example, pentachlorophenol is a potent wood preservative, pentabromophenol is a component of flame retardant formulations, 2,2'-methylenebis(3,4,6-trichlorophenol) is a potent and useful bactericide, and 4,4'-isopropylidenebis(2-chlorophenol) has been used as an anti-mildew agent. Often, derivatives of halophenols are also useful such as polymers derived from 4,4'-isopropylidenebis(2,6-dibromophenol) and the corresponding bis(dichlorophenol) which, in the form of polyesters and polycarbonates, possess outstanding flame-retardant characteristics as is known in the prior art.

The preparation of halophenols is customarily carried out by direct halogenation with elemental chlorine and/or bromine. In the case of simple or stable molecules, this appears to be the simplest process. However, when it is applied to more complicated and sensitive structures, it often yields by-products that can seriously interfere with the intended end-use of the halophenols. For instance, U.S. Pat. No. 3,062,781 discloses halogenated diphenols which are obtained by a direct halogenation procedure which require further treatment with sodium hydroxide and triethylamine at 80° C. before they can be converted to polycarbonates of acceptable stability. Such a treatment is necessary in order to remove aliphatically bound halogens formed in the halogenation process. It has been found that these aliphatically bound halogen compounds, which are generally recognizable by their red color, are formed by the cleavage reaction exerted by the hydrogen halide coproduct on the diphenol. For example, when 4,4'-isopropylidenediphenol (BPA) is employed, the chlorination reaction produces an equimolar amount of hydrogen chloride coproduct as shown below:

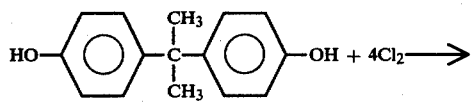
(I)

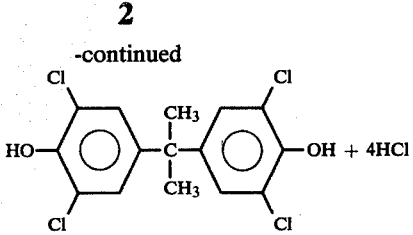

The HCl coproduct produced in (I) above effects a cleavage reaction on BPA or its chlorinated derivatives as shown below:

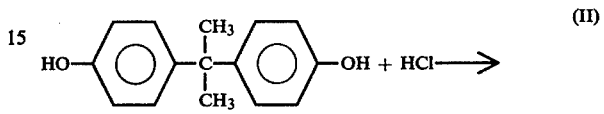
(II)

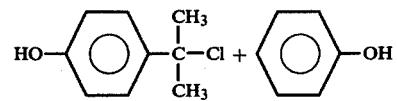

or

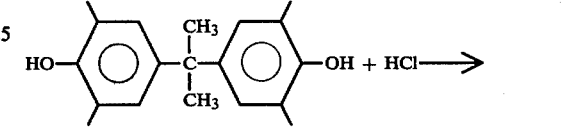
(III)

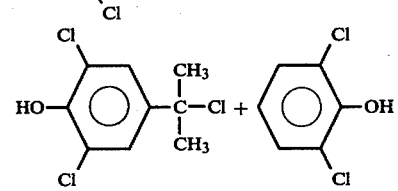

Thus, the chloroisopropylphenols cause the discoloration and the chlorinated phenols also have a disagreeable odor. The formation of by-products is even more pronounced in bromination processes.

German Patent No. P25 20 317.2 discloses two methods for brominating and/or chlorinating bisphenols; namely, a gas-solid phase method and a suspension method. From these methods, there are obtained a mixture of unreacted bisphenol and statistical mixtures of halogenated bisphenols which are used to prepare polycarbonates having improved fire retardant properties.

In the suspension method disclosed in this German patent, the bisphenol is suspended in a halogen-containing hydrocarbon to produce a halogenated bisphenol. The halogen-containing hydrocarbons disclosed are carbon tetrachloride and tetrachloroethane, carbon tetrachloride being preferred.

While the suspension method disclosed in the above-identified German patent is of interest, it is not entirely satisfactory. For example, since bisphenols are not very soluble in either carbon tetrachloride or tetrachloroethane, excess halogen, i.e., either bromine and/or chlorine, must be used to assure halogenation of the bisphenols. As a result, a significant amount of halogen is lost in the system during the reaction and the rate of halogenation cannot be closely controlled. Thus, this method produces an excess of unreacted bisphenols and, primarily, tri- and tetrahalogenated bisphenols which, when further processed to produce a polycarbonate, do not impart good impact properties to the polycarbonate. Furthermore, the halogenated bisphenols must be isolated from the solvent system before they can be subjected to polymerization to obtain polycarbonates.

Co-pending application Ser. No. 882,192, filed Feb. 28, 1978 and assigned to the same assignee as this case discloses a continuous process for producing high molecular weight polycarbonates including halogenating diphenols wherein the diphenol is dissolved or suspended in a solvent system comprising methylene chloride and water and metering a halogen gas into the solvent system. In that process, water is used to react with the hydrogen halide produced and thereby minimize the formation of undesirable by-products.

Co-pending application Ser No. 882,191, filed Feb. 28, 1978, also assigned to the same assignee as this case, discloses a process for halogenating diphenols wherein the diphenol is dissolved or suspended in methylene chloride and then contacted with a halogen while the reaction is concurrently purged with an inert gas. The inert gas serves to sweep out the hydrogen halide produced during the reaction thereby minimizing the formation of undesirable by-products.

SUMMARY OF THE INVENTION

It has now been found that halogenated diphenols obtainable in high purity can be prepared by suspending or dissolving the diphenol in a suitable solvent such as methylene chloride and thereafter reacting the diphenol with sulfuryl chloride. Other halogens such as bromine can also be concurrently introduced into the reaction system to provide a mixture of halogens and thereby obtain a halogenated diphenol having a predetermined degree of halogen content and containing a negligible amount of deleterious by-products. Since this process results in minimizing impurities as well as minimizing the formation of undesirable by-products, the highly pure halogenated diphenol obtained need not be treated further before being used. These halogenated diphenols can be used as anti-mildew agents, fungicides, fire retardant agents in various polyesters, monomers for the preparation of aromatic polycarbonates, and the like.

The process of this invention can be made continuous and is based on using quantitative amounts of reactants thereby enabling the extent of halogenation to be closely controlled. As a result, all of the halogen employed is reacted with the diphenol so that there is realized not only a savings in material and labor cost, but a savings in time as well as increased product yield. Accordingly, the process of the invention can be adapted for use with other processes to continuously produce such materials as fire retardant polyesters, aromatic polycarbonates, and the like.

Methylene chloride in the solvent system of the present invention is employed in amounts sufficient to result in a clear solution when the halogenation reaction is complete.

Use of sulfuryl chloride as the halogenating agent with such acid sensitive materials results in preventing or minimizing the deleterious effect of the hydrogen halide produced during the reaction which, in turn, can result in the formation of undesirable by-products. During the reaction, the sulfuryl chloride generates a gas, sulfur dioxide, in situ which is neutral to the reaction and which serves to purge the reaction of the hydrogen halide coproduct before this coproduct can effect side reactions. Thus, chlorinations using sulfuryl chloride are "self sweeping" and result in producing products of high purity. The following equation exemplifies the reaction of the process of the invention using, as the diphenol, bisphenol-A; i.e., 4,4'-isopropylidenediphenol (BPA):

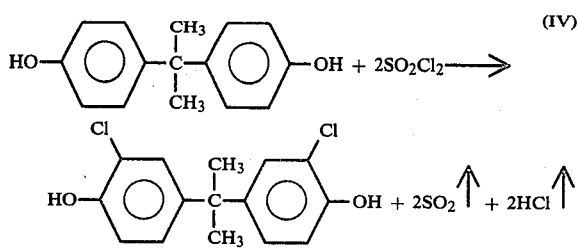

Thus, the improvement over chlorination with elemental chlorine is readily recognizable by the formation of essentially colorless solutions and the absence of the characteristic, strong odor of chlorophenols.

By minimizing the undesirable hydrogen halide coproduct, HX, the formation of deleterious by-products, illustrated by the following general equation, are also minimized:

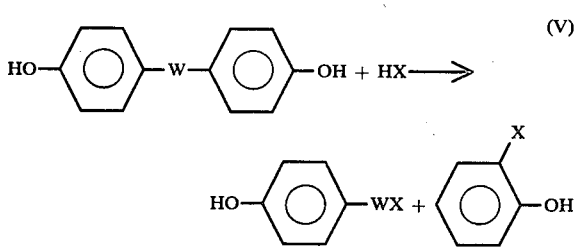

Accordingly, the halogenated diphenols produced using the process of this invention can be represented by the following general formula:

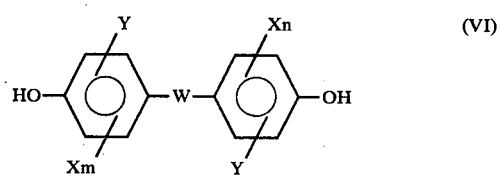

wherein $X_m$ and $X_n$ are chlorine, bromine, and mixtures thereof with the proviso that either $X_m$ or $X_n$ is chlorine; Y is independently selected from the group consisting of $C_1$–$C_4$ alkyl and hydrogen; m and n are each 0–2 with the proviso that m+n equal at least 0.1, but no more than 2; and, W is a member selected from the following group:

(a) $-(CH_2)_r-$ wherein r is an integer of 0–10 with the proviso that when both $X_m$ and $X_n$ are chlorine and m and n are each 1, r is 0 or 2–10;

(b)

wherein R is a member of the group consisting of $C_1$–$C_{10}$ alkyl and $C_6$–$C_{14}$ aryl;

(c)

wherein R and R' can each independently be the same as R in (b) above;

(d)

wherein p and q can each independently be 0-1; and, (e) —O—.

W and X are the same in the formulas for equations V as described for formula VI.

In producing the diphenol of formula VI wherein W can be (a), (b) or (c), particularly (c), the formation of deleterious by-products is especially pronounced when employing prior art processes. When the process of this invention is employed, however, the formation of such deleterious by-products is dramatically minimized and virtually eliminated. Thus, the halogenated diphenols produced in accordance with this invention are virtually colorless or white as compared to the discolored halogenated diphenols obtained by prior art processes.

The temperature of the halogenation reaction can be about 0°-80° C., but is preferably held at about ambient temperature; i.e., 20°-35° C.

The amount of halogen added can vary depending upon the extent of halogenation desired. Thus, halogen can be added in amounts of about 0.1-2 moles per mole of diphenol employed.

Since the reaction in the process of the invention is based upon quantitative consumption of halogen, the process enables the degree of halogenation of the diphenol to be closely controlled. Accordingly, predetermined statistical mixtures of unreacted diphenol and reacted diphenol can be readily obtained. The amount of each obtained depends upon the moles of halogen added. This is illustrated by the graphic correlation diagram shown in the single diagrammatic FIGURE in the drawing.

As can be seen from the diagram in the drawing, a statistical maximum of 50 mole percent of monohalodiphenol obtains at a mole ratio of halogen:diphenol of 1:1, whereas a statistical maximum of essentially 100 mole percent dihalodiphenol obtains at a mole ratio of halogen:diphenol of 2:1. Accordingly, it is possible to produce essentially 100% of pure dihalodiphenol. Alternatively, statistical ternary mixtures comprising unreacted diphenol, monohalodiphenol and dihalodiphenol can be obtained as shown by the above diagram. This also pertains when mixtures of halogens are employed.

Typical of some of the diphenols that can be employed in this invention are disphenol-A (2,2-bis(4-hydroxyphenyl)propane, also referred to as 4,4'-isopropylidenediphenol), bis(4-hydroxyphenyl)-methane, 2,2-bis(4-hydroxy-3-methylphenyl)propane, 4,4-bis(4-hydroxyphenyl)heptane, 1,1-bis(4-hydroxyphenyl)ethane, 3-methyl-2,2-bis(4-hydroxyphenyl)propane, bis(4-hydroxyphenyl)sulfone, bis-(4-hydroxyphenyl)ether, and the like. Other non-halogenated diphenols of the bisphenol type can also be used such as are disclosed in U.S. Pat. Nos. 2,999,835, 3,028,365 and 3,334,154.

PREFERRED EMBODIMENT OF THE INVENTION

The following examples are set forth to more fully and clearly illustrate the present invention and are intended to be, and should be construed as being, exemplary and not limitative of the invention. Unless otherwise stated, all parts and percentages are by weight.

EXAMPLE 1

To a slurry of 684 g (3.0 moles) of 4,4'-isopropylidenediphenol, (BPA) in 2000 ml of methylene chloride was added, dropwise at ambient temperature, 810 g (6.0 moles) of sulfuryl chloride. Copious evolution of hydrogen chloride and sulfur dioxide soon ensued, accompanied by gradual warming of the slurry to 35° C. and refluxing of the solvent. The addition of sulfuryl chloride required about 6 hours, by which time most of the BPA became dissolved. After one hour of refluxing by the application of external heat, the clear solution was sampled for gas chromatographic analysis. (6'×1/8" stainless steel, 5% Silicon OV-101 on Anakrom ABS (acrylonitrile-butadiene-styrene) column, 80°-330° C. range, programmed at 8° C./minute). This indicated by matching, after trimethylsilylation with bis(trimethylsilyl) trifluoroacetamide, the correct retention times of authentic reference samples, the following composition:

| | Retention Time (min.) | Composition (mole %) |
|---|---|---|
| 4,4'-isopropylidenediphenol | 17.1 | 0.9 |
| 2-chloro-4,4'-isopropylidenediphenol | 18.3 | 7.5 |
| 2,2'-dichloro-4,4'-isopropylidenediphenol | 19.8 | 93.6 |
| 2,2',6-trichloro-4,4'-isopropylidenediphenol | 20.8 | 1.0 |
| 2,2',6,6'-tetrachloro-4,4'-isopropylidenediphenol | 22.6 | 0.0 |
| Reference (p-cumylphenol) | 13.0 | |

To increase the dihalodiphenol content of the preparation and replace the sulfuryl chloride that had been swept out of the system by the evolving gases, 27.8 g (0.28 mole) of sulfuryl chloride was added within 30 minutes to the original solution, which then was heated to reflux for 3 hours and sampled for an additional gas chromatographic analysis, which showed the following composition:

| Composition | Composition (mole %) |
|---|---|
| 4,4'-isopropylidenediphenol | 0.4 |
| 2-chloro-4,4'-isopropylidenediphenol | 3.2 |
| 2,2'-dichloro-4,4'-isopropylidenediphenol | 96.0 |
| 2,2',6-trichloro-4,4'-isopropyliedenediphenol | 1.2 |
| 2,2',6,6'-tetrachloro-4,4'-isopropylidenediphenol | 0.0 |

The solution was added to 3 liters of water, stirred and the crystals that formed were filtered through a sintered glass suction funnel, rinsed twice with water and air dried. The pure white crystals of 2,2'-dichloro-4,4'-isopropylidenediphenol trihydrate were obtained in 1053 g or essentially quantitative yield and showed a 97.2% assay in this compound. The high purity was also confirmed by its melting point of 90.5°-92.0° C. Infrared, ultraviolet, proton and $^{13}$C-nmr also confirmed both the purity and the structure of the product.

EXAMPLE 2

The procedure of Example 1 was repeated, except that only half as much sulfuryl chloride (3.0 moles) but twice as much methylene chloride were used. Gas chromatographic analysis of the reaction sample, after the addition of the chlorinating agent and one hour reflux, indicated the following composition:

| Compound | Composition (mole %) |
| --- | --- |
| 4,4'-isopropylidenediphenol | 27.2 |
| 2-chloro-4,4'-isopropylidenediphenol | 49.0 |
| 2,2'-dichloro-4,4'-isopropylidenediphenol | 23.7 |
| 2,2',6-trichloro-4,4'-isopropylidenediphenol | 0.1 |

This composition thus corresponded very closely to the theoretical, ideally random statistical distribution, which is 25:50:25%, unreacted BPA:monochloro BPA:-dichloro BPA. Gas chromatographic analysis indicated the essential absence of by-products and that the original reaction mixture which, on water treatment, yielded colorless crystals, could be directly utilized for the prepartion of a corresponding statistical mixture of polycarbonates.

Furthermore, the statistical composition that was maximized to the monochloro compound, could be worked up, if so desired, by selective recrystallization and the pure 2-chloro-4,4'-isopropylidenediphenol can be isolated in high purity with a melting point of 105.5°-107° C.

By contrast, an analogous statistical mixture obtained by direct chlorination, as shown in Example 3 below, yielded a pink or redish reaction mixture that had to be extensively purified by treatment with alkali and/or recrystallization, thus destroying the statistically random composition before it could be utilized for the preparation of polycarbonates of acceptable purity and reproducible composition.

EXAMPLE 3

The procedure of Example 2 was repeated, except that the chlorination was carried out with an equivalent amount of elemental chlorine (3.0 moles) instead of sulfuryl chloride. As the chlorination progressed, the solution turned gradually pink then deep red and, concomitantly, the characteristic odor of chlorophenols gradually developed. As the reaction mixture was sampled for chromatographic analyses, the formation of significant amounts of by-products as the chlorination was finished was confirmed by the presence of 0.1–1.2% chlorophenols and higher boiling impurities which preceded the emergence of chloro-BPA's.

EXAMPLE 4

To a solution of 134.2 g (0.5 mole) of 4,4'-cyclohexylidenediphenol in 1900 ml of refluxing benzene was added gradually 135.0 g (1.0 mole) of sulfuryl chloride in the course of 5 hours. After an additional one hour of reflux, the yellow solution was sampled for gas chromatographic analysis, which indicated the following composition:

| | Retention Time (min.) | Composition (mole %) |
| --- | --- | --- |
| 4,4'-cyclohexylidenediphenol | 19.57 | 0.0 |
| 2-chloro-4,4'-cyclohexylidenediphenol | 20.82 | 10.3 |
| 2,2'-dichloro-4,4'-cyclohexylidenediphenol | 23.15 | 89.7 |
| Reference (4-cumylphenol) | 12.36 | |

Workup by treatment with water, filtration and rinsing yielded 161.5 g of white crystals which, after recrystallization from methylene chloride, contained 98.9% di-, 0.4% mono- and 0.7% thrichloro-4,4'-cyclohexylidenediphenol and had a melting point of 143°-145° C.

EXAMPLE 5

The procedure of Example 3 was repeated, except that only 81.0 g (0.6 mole) of sulfuryl chloride was employed. Gas chromatographic analysis at the end of the reaction indicated a nearly random statistical distribution:

| Compound | Composition (mole %) |
| --- | --- |
| 4,4'-cyclohexylidenediphenol | 16.0 |
| 2-chloro-4,4'-cyclohexylidenediphenol | 47.2 |
| 2,2'-dichloro-4,4'-cyclohexylidenediphenol | 36.8 |

EXAMPLE 6

The procedure of Example 1 was repeated on the one molar scale by using 214.3 g (1.0) mole) of 4,4'-ethylidenediphenol, 1 L of methylene chloride and 270.0 g (2.0 moles) of sulfuryl chloride. Gas chromatography indicated the following composition:

| | Retention Time (min.) | Composition (mole %) |
| --- | --- | --- |
| 4,4'-ethylidenediphenol | 19.87 | 0.1 |
| 2-chloro-4,4'-ethylidenediphenol | 21.21 | 17.0 |
| 2,2'-dichloro-4,4'-ethylidenediphenol | 22.68 | 82.2 |
| 2,2',6-trichloro-4,4'-ethylidenediphenol | 23.02 | 0.2 |
| Reference (p-cumylphenol) | 16.43 | |

EXAMPLE 7

The procedure of Example 1 was repeated except that a slurry of 196.2 g (0.668 m) of 4,4'-(2,2,2-trichloroethylidene) in diphenol 300 ml of methylene chloride was chlorinated with 183 g (1.356 mole) of sulfuryl chloride between 21° and 36° C. Workup of the reaction mixture by filtering off undissolved starting material (75.9 g or 0.26 mole) yielded 165.3 g of a light brown oil with the following composition:

| Compound | Retention Time (min.) | Composition (mole %) |
| --- | --- | --- |
| 4,4'-(2,2,2-trichloroethylidene)diphenol | 20.02 | 0.1 |
| 2-chloro-4,4'-(2,2,2-trichloroethylidene)-diphenol | 21.14 | 0.6 |
| 2,2'-dichloro-4,4'-(2,2,2-trichloroethylidene)diphenol | 22.03 | 50.7 |
| 2,2',6-trichloro-4,4'-(2,2,2-trichloroethylidene)diphenol | 22.97 | 46.0 |
| 2,2',6,6'-tetrachloro-4,4'-(2,2,2-trichloroethylidene)diphenol | 23.84 | 2.6 |

| Compound | Retention Time (min.) | Composition (mole %) |
|---|---|---|
| Reference (p-cumylphenol) | 12.58 | |

EXAMPLE 8

The procedure of Example 1 was repeated except that to a slurry of 50.0 g (0.178 mole) of 4,4'-(dichlorovinylidene)diphenol in 3 L of methylene chloride was added 50.0 g (0.37 mole) of sulfuryl chloride in the course of one hour, at which time all of the diphenol was in solution. The refluxing of the solution was continued by the application of external heat until gas evolution ceased. Workup of the reaction mixture, as described in Example 1, yielded white crystals, for which gas chromatography indicated the following composition:

| Compound | Retention Time (min.) | Composition (mole %) |
|---|---|---|
| 4,4'-(dichlorovinylidene)diphenol | 18.97 | 0.2 |
| 2-chloro-4,4'-(dichlorovinylidene)diphenol | 20.11 | 18.5 |
| 2,2'-dichloro-4,4'-(dichlorovinylidene)-diphenol | 20.91 | 81.1 |
| 2,2',6-trichloro-4,4'-(dichlorovinylidene)-diphenol | 21.91 | 0.2 |
| 2,2',6,6'-tetrachloro-4,4'-(dichlorovinylidene)diphenol | 22.87 | 0.0 |
| Reference (p-cumylphenol) | 12.36 | |

Recrystallization of the white solids from hexane yielded colorless crystals of the 2,2'-dichloro-4,4'-(dichlorovinylidene)diphenol, mp. 109°–110.5° C., and an assay of 98.0%.

EXAMPLE 9

The procedure of Example 1 was repeated, except that a slurry of 50.5 g (0.25 mole) of 4,4'-oxydiphenol in 3 L of methylene chloride was chlorinated with 68.0 g (0.5 mole) of sulfuryl chloride. After the evolution of gases ceased, the colorless solution was sampled for gas chromatographic analysis which showed the following composition:

| Compound | Retention Time (min.) | Composition (mole %) |
|---|---|---|
| 4,4'-oxydiphenol | 18.15 | 0.0 |
| 2,2'-dichloro-4,4'-oxydiphenol | 20.97 | 94.0 |
| 2,2',6-trichloro-4,4'-oxydiphenol | 22.23 | 6.0 |

Recrystallization of the white solids from methylene chloride yielded colorless crystals of 2,2'-dichloro-4,4'-oxydiphenol, mp 113°–114° C., which were 98.1% pure by gas chromatography.

EXAMPLE 10

The procedure of Example 1 was repeated, except that a thin slurry of 296 g (1.0 mole) of 2,2'-dimethyl-4,4'-cyclohexylidenediphenol in 10 L of methylene chloride was chlorinated with 270 g (2.0 moles) of sulfuryl chloride in the course of 4 hours. Gas chromatographic analysis indicated the following composition:

| Compound | Retention Time (min.) | Composition (%) |
|---|---|---|
| 2,2'-dimethyl-4,4'-cyclohexylidenediphenol | 22.72 | 8.6 |
| 6-chloro-2,2'-dimethyl-4,4'-cyclohexylidenediphenol | 24.01 | 7.1 |
| 6,6'-dichloro-2,2'-dimethyl-4,4'-cyclohexylidenediphenol | 25.44 | 84.3 |

The structures of the new compounds described above were confirmed by proton nmr analyses, which yielded correct integrated areas for the aliphatic and aromatic protons and the absence of chloromethylated derivatives. The pure product, 2,2'-dichloro-4,4'-cyclohexylidenedi-o-cresol, was obtained in 98.8% purity with a 136.5°–137.5° C. mp after recrystallization from the water-methanol mixture.

As mentioned earlier, the process disclosed in German Patent No. P25 20 317.2 results in producing a mixture of unreacted bisphenol and statistical mixtures of halogenated bisphenol whereas the process of this invention, as shown by the foregoing examples, results in producing true statistical mixtures comprising unreacted bisphenol, monohalobisphenol and dihalobisphenol.

What is claimed is:

1. A process for obtaining halogenated diphenols comprising:
   dissolving or suspending a diphenol of the bisphenol type in methylene chloride; and,
   introducing sulfuryl chloride into said diphenol and methylene chloride in an amount sufficient to provide about 0.1–2 moles chlorine per mole of diphenol, said sulfuryl chloride generating sulfur dioxide which purges the reaction of halogen halide co-product such that there is obtained therefrom either a substantially pure dihalodiphenol or a statistical ternary mixture consisting essentially of unreacted diphenol, monohalodiphenol and dihalodiphenol.

2. The process of claim 1 wherein bromine is concurrently introduced into said diphenol and methylene chloride with said sulfuryl chloride.

3. The process of claim 1 wherein said diphenol is a member selected from the group of diphenols represented by the general formula:

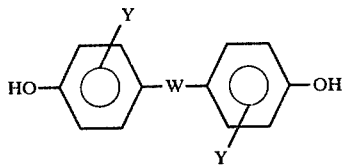

wherein Y is a member independently selected from the group consisting of $C_1$–$C_4$ alkyl and hydrogen; and, W is a member selected from the following group:
(a) $-(CH_2)_r-$ wherein r is an integer of 0–10;
(b)

wherein R is a member of the group consisting of $C_1$–$C_{10}$ alkyl and $C_6$–$C_{14}$ aryl;

(c)

wherein R and R' can each independently be the same as R in (b) above;

(d)

wherein p and q can each independently be 0–1; and, (e) —O—.

4. The process of claim 3 wherein said diphenol is 2,2'bis-(4-hydroxyphenyl) propane.

5. The process of claim 1 wherein the amount of halogen incorporated is about 1.5 moles per mole of said diphenol.

6. The process of claim 1 wherein the amount of halogen incorporated is no more than 2.0 moles per mole of said diphenol.

7. The halogenated diphenol of claim 3 wherein Y is hydrogen.

8. The halogenated diphenol of claim 3 wherein Y is $CH_3$.